(12) United States Patent
Liu

(10) Patent No.: US 11,918,738 B2
(45) Date of Patent: Mar. 5, 2024

(54) ELECTRONIC CIGARETTE AND METHOD FOR MANUFACTURING ATOMIZING ASSEMBLY THEREOF

(71) Applicant: Shenzhen Smoore Technology Limited, Guangdong (CN)

(72) Inventor: Pingkun Liu, Guangdong (CN)

(73) Assignee: Shenzhen Smoore Technology Limited, Shenzhen (CN)

(*) Notice: Subject to any disclaimer, the term of this patent is extended or adjusted under 35 U.S.C. 154(b) by 20 days.

(21) Appl. No.: 17/889,548

(22) Filed: Aug. 17, 2022

(65) Prior Publication Data

US 2022/0387739 A1 Dec. 8, 2022

Related U.S. Application Data

(63) Continuation of application No. 17/004,123, filed on Aug. 27, 2020, now Pat. No. 11,446,452, which is a continuation of application No. 15/740,657, filed as application No. PCT/CN2015/092421 on Oct. 21, 2015, now Pat. No. 10,791,762.

(51) Int. Cl.
*A24F 40/10* (2020.01)
*A24F 40/44* (2020.01)
*A24F 40/46* (2020.01)
*A24F 40/70* (2020.01)
*A61M 11/04* (2006.01)
*A61M 15/06* (2006.01)

(52) U.S. Cl.
CPC .............. *A61M 15/06* (2013.01); *A24F 40/44* (2020.01); *A24F 40/46* (2020.01); *A24F 40/70* (2020.01); *A61M 11/042* (2014.02); *A24F 40/10* (2020.01); *A61M 2205/0211* (2013.01)

(58) Field of Classification Search
CPC .......... A24F 40/10; A24F 40/44; A24F 40/46; A24F 40/70; A61M 11/042; A61M 15/06; A61M 2205/0211
See application file for complete search history.

(56) References Cited

U.S. PATENT DOCUMENTS 9,572,373 B2 * 2/2017 Chen ..................... A61M 15/06
9,861,132 B2 * 1/2018 Li ............................ A24F 40/46
10,524,514 B2 * 1/2020 Cyphert ................. H05B 6/105
(Continued)

*Primary Examiner* — Abdullah A Riyami
*Assistant Examiner* — Thang H Nguyen
(74) *Attorney, Agent, or Firm* — COATS & BENNETT, PLLC

(57) ABSTRACT

An electronic cigarette and a method for manufacturing an atomizing assembly thereof. The electronic cigarette comprises a liquid reservoir used for storing an e-liquid, and an atomizing assembly received in a shell. The atomizing assembly comprises: a liquid-absorbing element connected to the liquid reservoir, wherein the liquid-absorbing element is made of porous ceramic, and has a liquid-absorbing surface for absorbing the e-liquid and an atomizing surface; and a heating element embedded in the liquid-absorbing element, wherein the edge of the heating element is internally tangent to the atomizing surface, and the heating element is used for converting the e-liquid absorbed by the liquid-absorbing element into smoke. The electronic cigarette further comprises a power supply assembly received in the shell, connected to the atomizing assembly, and used for supplying power for the heating element.

14 Claims, 13 Drawing Sheets

(56) References Cited

U.S. PATENT DOCUMENTS

| | | | |
|---|---|---|---|
| 2012/0279512 A1* | 11/2012 | Hon | A24F 40/42 |
| | | | 131/329 |
| 2013/0192623 A1* | 8/2013 | Tucker | H05B 3/16 |
| | | | 131/329 |
| 2013/0255675 A1* | 10/2013 | Liu | A61M 11/041 |
| | | | 128/202.21 |
| 2014/0150785 A1* | 6/2014 | Malik | A61M 11/042 |
| | | | 128/202.21 |
| 2015/0272218 A1* | 10/2015 | Chen | A61M 15/06 |
| | | | 131/329 |
| 2016/0366943 A1* | 12/2016 | Li | A24F 40/42 |
| 2017/0224018 A1* | 8/2017 | Li | A24F 40/46 |
| 2020/0054075 A1* | 2/2020 | Zhang | A24F 40/44 |
| 2021/0227885 A1* | 7/2021 | Sudlow | A61M 11/04 |

\* cited by examiner

ELECTRONIC CIGARETTE AND METHOD FOR MANUFACTURING ATOMIZING ASSEMBLY THEREOF

CROSS-REFERENCE TO RELATED APPLICATIONS

This application is a continuation application of U.S. patent application Ser. No. 17/004,123, filed Aug. 27, 2020, entitled, "ELECTRONIC CIGARETTE AND METHOD FOR MANUFACTURING ATOMIZING ASSEMBLY THEREOF", which is a continuation application of U.S. patent application Ser. No. 15/740,657, filed Dec. 28, 2017 entitled, "ELECTRONIC CIGARETTE AND METHOD FOR MANUFACTURING ATOMIZING ASSEMBLY THEREOF", now U.S. Pat. No. 10,791,762, which itself is a national stage application under 35 U.S.C. 371 of PCT Application No. PCT/CN2015/092421 having an international filing date of Oct. 21, 2015, the contents of which are incorporated by reference herein in their entirety for all purposes.

FIELD OF THE INVENTION

The present disclosure relates to an electronic cigarette and a method for manufacturing an atomizing assembly thereof.

BACKGROUND OF THE INVENTION

Electronic cigarette, also known as virtual cigarette or electronic atomizers, is a substitute of the cigarette for smoking cessation. The electronic cigarette has a similar appearance and taste as the cigarette, but it generally does not contain other harmful ingredients in the cigarettes, such as tar, suspended particles, and so on.

The electronic cigarette is usually composed of an atomizer and a power supply assembly. The atomizer is a core unit of the electronic cigarette for generating an atomizing gas, and its atomization effect determines the quality and taste of the smoke. A conventional heating element of the atomizer is a spring-like heating wire, which is fabricated by winding a linear heating wire around a wick. The smoking liquid in the liquid storage device is adsorbed to the wick through both ends of the wick and then heated and atomized by the heating wire. However, the liquid of this type of electronic cigarette is completely absorbed by both ends of the wick and then atomized. Due to the limited area of the end of the wick, the adsorption efficiency of the liquid is quite low. Therefore, when a high power heating wire is used, there will be inadequate liquid supply to the wick, thus resulting in dry burning as well as production of a burning smell.

To address the aforementioned inadequate liquid supply issue, the improvement in the prior art is that the helical heating wire is externally coated with a liquid guiding structure such as liquid guiding cotton, such that the whole sidewall of the liquid guiding cotton can be used to conduct liquid, thus providing adequate liquid supply. However, this approach suffers from some problems, such as: 1) a popping sound by the liquid is often produced; and 2) the atomizing efficiency is low, i.e., the amount of atomized smoke is relatively small at the same power.

SUMMARY OF THE INVENTION

Accordingly, it is necessary to provide an electronic cigarette with a better atomizing effect.

An electronic cigarette includes:
a liquid reservoir configured to store liquid;
an atomizing assembly received in the housing, the atomizing assembly comprising:
  a liquid absorption element connected to the liquid reservoir, the liquid absorption element being made of porous ceramic, and the liquid absorption element having a liquid absorption surface configured to absorb the liquid, and an atomizing surface; and
  a heating element embedded in an interior of the liquid absorption element, wherein an edge of the heating element is internally tangent to the atomizing surface, and the heating element is configured to atomize the liquid absorbed by the liquid absorption element into atomized gas; and
a power source assembly received in the housing and connected to the atomizing assembly, the power source assembly being configured to provide power for the heating element.

A method of manufacturing an atomizing assembly includes:
providing a positioning element, the positioning element comprising a positioning post;
winding a heating element spirally around the positioning post;
placing the positioning post wound with the heating element into a mold, injection molding a first layer of ceramic material on a surface of the heating element and then curing;
removing the positioning post from the cured first layer of ceramic material; and
sintering the cured first layer of ceramic material, thus obtaining a liquid absorption element made of porous ceramic and a heating element embedded in an interior of the liquid absorption element.

An electronic cigarette includes:
a liquid reservoir received in the housing and configured to store liquid;
an atomizing assembly received in the housing, the atomizing assembly comprising:
  a support element defining an atomizing passage therein, the support element defining two aligned through holes on a sidewall thereof in communication with the atomizing passage;
  a liquid absorption element made of porous ceramic, wherein both ends of the liquid absorption element extend through the through holes and extend inside the liquid reservoir, the liquid absorption element having a liquid absorption surface configured to absorb the liquid and an atomizing surface located inside the atomizing passage; and
  a heating element embedded in an interior of the liquid absorption element, wherein an edge of the heating element is internally tangent to the atomizing surface, and
a power source assembly received in the housing and connected to the atomizing assembly, the power source assembly being configured to provide power for the heating element.

Compared with the prior art, the heating element is completely embedded in an interior of the liquid absorption element, while the liquid absorption element made of porous ceramic is full of liquid, therefore, the heating element is in complete contact with the liquid and achieves a better atomizing effect.

BRIEF DESCRIPTION OF THE DRAWINGS

The above objects, features and advantages of the present invention will become more apparent by describing in detail embodiments thereof with reference to the accompanying drawings. The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION OF THE EMBODIMENTS

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present. Additionally, the words "herein", "above", "below" and words of similar import, when used in this application, shall refer to this application as a whole and not to any particular portions of this application.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
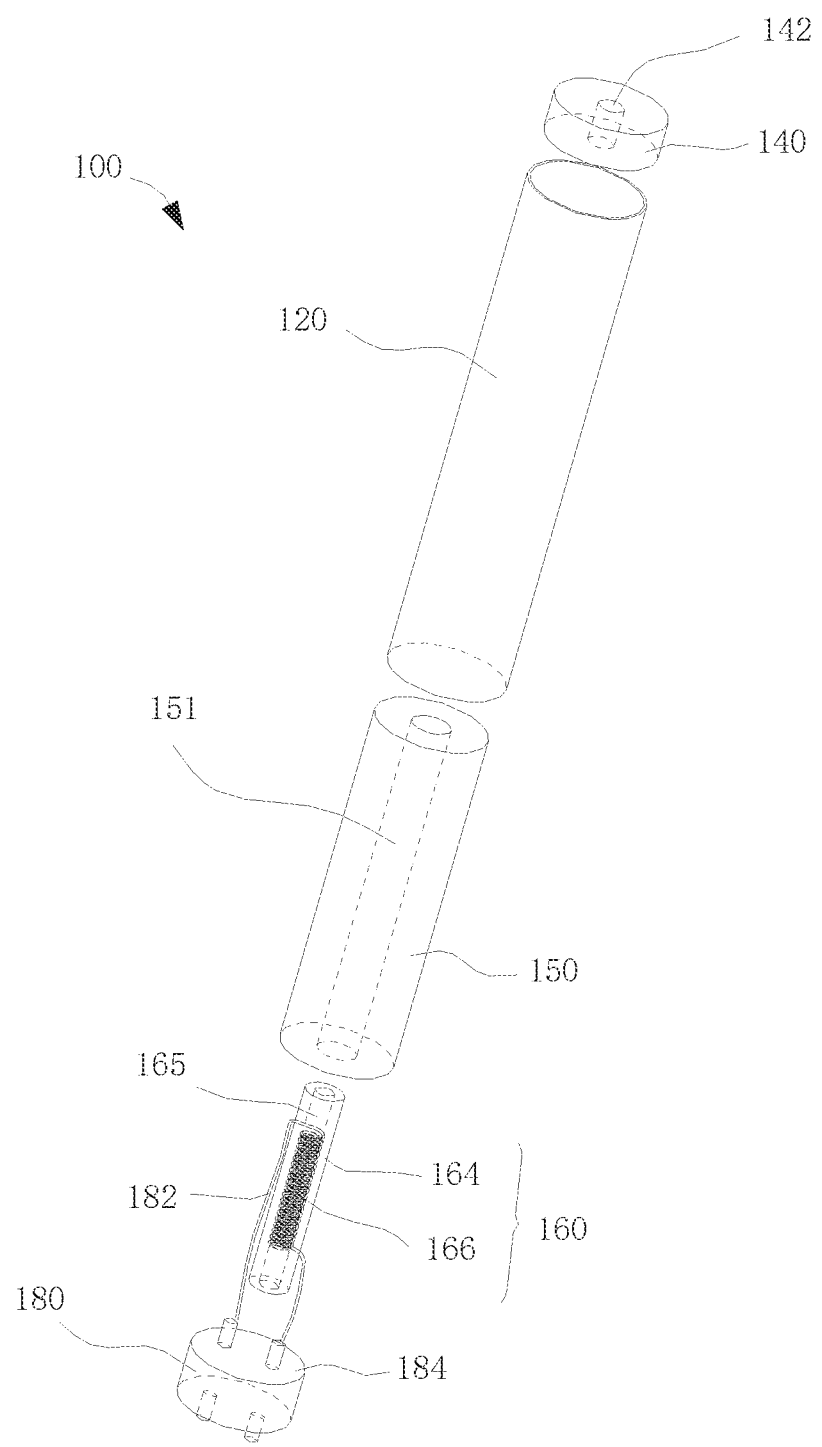
FIG. 1 is a perspective view of an electronic cigarette according to a first embodiment.
Figure 2:
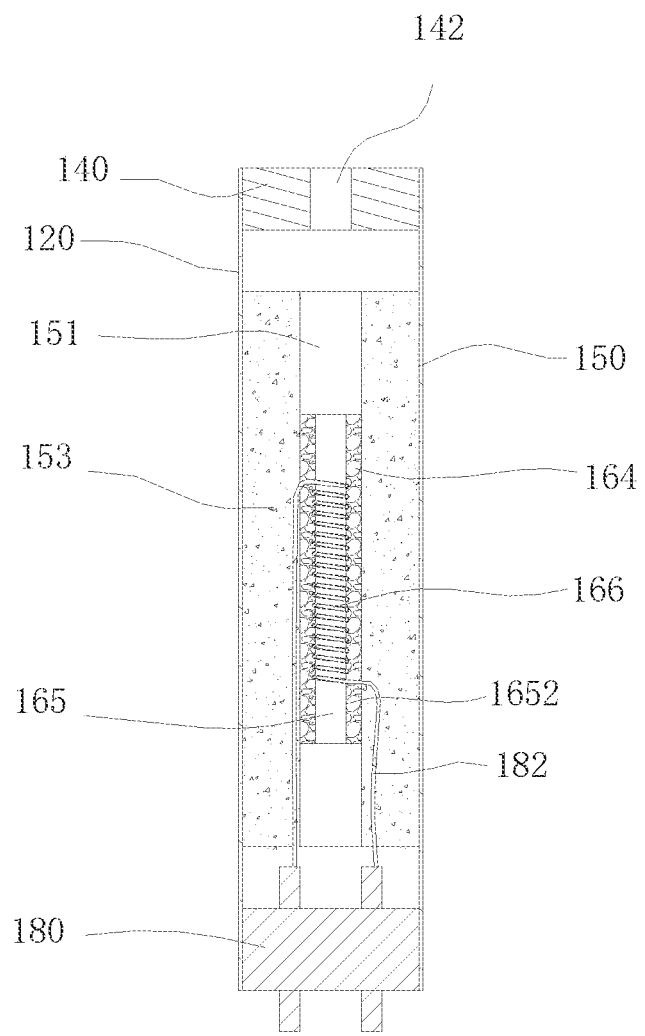
FIG. 2 is a cross-sectional view of the electronic cigarette of FIG. 1.

Referring to FIG. 1 and FIG. 2, an electronic cigarette 100 in accordance with a first embodiment includes a housing 120, a mouthpiece 140, a liquid reservoir 150, an atomizing assembly 160, and a power source assembly 180.

The housing 120 is substantially a hollow elongated cylinder. The mouthpiece 140 is located at an end of the housing 120, and the atomizing assembly 160 and the power source 180 are received inside the housing 120. It is to be understood that, the housing 120 may have other shapes, such as rectangular or the like.

The mouthpiece 140 has thread on its outer periphery, and the mouthpiece 140 is threadedly fixed at the top of the housing 120. The mouthpiece 140 defines an air outlet 142 at a center thereof. It should be understood that, the mouthpiece 140 can be omitted.

The liquid reservoir 150 is substantially a hollow circular tube and is mainly used for storing liquid. The liquid reservoir 150 internally defines a substantially cylindrical channel 151 along an axial direction thereof. The channel 151 is aligned with the air outlet 142. The liquid reservoir 150 is filled with a storage medium 153 for storing liquid. The storage medium 153 can be made of fibers, preferably modified fibers, which can remove the odor of the liquid, so as not to affect the taste of the smoke.

The atomizing assembly 160 includes a liquid absorption element 164, and a heating element 166.

The liquid absorption element 164 is connected to the liquid reservoir 150. In the illustrated embodiment, the liquid absorption element 164 is shaped as a tube matching with the channel 151. Accordingly, the liquid absorption element 164 can be inserted into the channel 151 of the liquid reservoir 150 and be in direct contact with the storage medium 153. The liquid absorption element 164 is made of porous ceramic material with liquid storage and heat-resisting features. Accordingly, the liquid from the storage medium 153 can be uniformly dispersed in the interior and surface of the liquid absorption element 164 by capillary action. The porosity of the porous ceramic forming the liquid absorption element 164 is 30% to 60%, preferably 35% to 45%. If the porosity is too high, the risk of leakage will be increased; if the porosity is too low, there will be insufficient liquid supply and other issues. The liquid absorption element 164 defines an internal atomizing passage 165 in an axial direction in communication with the channel 151. The liquid absorption element 164 has a liquid absorption surface 1642 contacting the storage medium 153 and configured to absorb the liquid. In the illustrated embodiment, the liquid absorption surface 1642 is an outer circumferential surface of the liquid absorption element 164. The liquid absorption element 164 further has an atomizing surface 1652 on the sidewall of the atomizing passage 165.

The heating element 166 is embedded in an interior of the liquid absorption element 164. In the illustrated embodiment, the heating element 166 is a spiral tubular heating wire, and an edge of the heating element 166 is internally tangent (aligned) to the atomizing surface 1652. The heating element 166 is made of a conductive material, such as flexible metals or alloys, preferably nichrome wire. When the heating element 166 is powered, the liquid absorption element 164 can be heated by the heating element 166, such that the liquid stored inside the liquid absorption element 164 will be uniformly heated and atomized into uniform vapor particles (i.e. smoke). The smoke enters the atomizing passage 165 through the atomizing surface 1652, and then enters the channel 151, and finally inhaled by the user via the air outlet 142.

In the conventional electronic cigarette, since the inner surface of the spiral heating wire is not be in direct contact with the liquid, it can only absorb very few liquid by capillary action or surface tension, which will lead to some problems, such as: a), once the heating wire is powered, the inner side temperature will rise instantaneously, burst sound will be produced upon in contact with the liquid (because the temperature of the liquid is low, the inside temperature of the heating wire is too high); b), during the atomization process, the attached liquid is too little, which results in a great temperature difference between the inner side and the outer side of the spiral heating wire. Since the temperature of the inner side of the heating wire is high, once the liquid is in contact with this hot area, the liquid may be cracked or chemical reaction may take place due to the high temperature, an formaldehyde gas may even be produced; c), when drawing by the user, the airflow temperature is higher due to the direct contact of the airflow with the inner side of the heating wire. Meanwhile, the heat on the inner side of the heating wire is wasted, thus resulting in a lower atomizing efficiency. However, in the illustrated embodiment, the heating element 166 is completely embedded inside the liquid absorption element 164, and the liquid absorption element 164 composed by porous ceramic is full of liquid, such that the heating element 166 is in complete contact with the liquid, which brings the following advantages: a), the inner surface and the outer surface of the spiral heating wire have a uniform temperature distribution; b), there is less waste of the heat; c), there is no or very few liquid crackle sound; d), no or very few formaldehyde or other harmful substance will be produced.

Figure 3A:
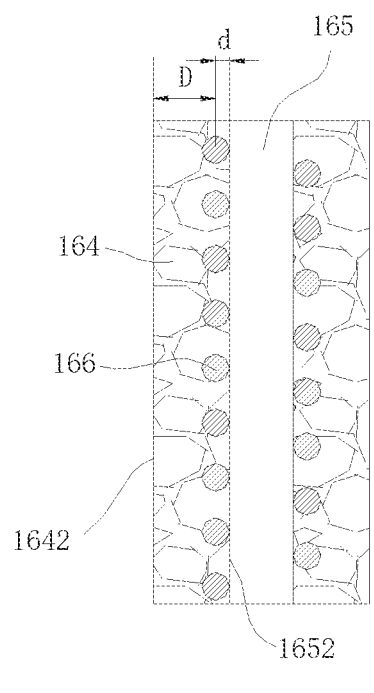
FIG. 3A is an enlarged cross-sectional view of an atomizing assembly according to an embodiment.

Referring to FIG. 3A, in one embodiment, the heating element 166 spirally surrounds the atomizing passage 165, and a distance d between the heating element 166 to the atomizing surface 1652 is less than a distance D between the heating element 166 to the liquid absorption surface 1642 of the liquid absorption element 164. Therefore, the liquid absorption surface 1642 of the liquid absorption element 164 composed of porous ceramic has a lower temperature and does not transfer too much heat to the liquid in the liquid reservoir 150, thus avoiding the temperature rise of the liquid which is not atomized. Or else, the energy is wasted on the one hand, and it is on the other hand inconvenient for the user to hold. In an alternative embodiment, a thermal conductivity of the liquid absorption element is gradually reduced from inside to outside along a radial direction, which can also reduce the surface temperature of the electronic cigarette.

According to an embodiment, a method of manufacturing an atomizing assembly includes the following steps:

In step one, a positioning element is provided, the positioning element has a positioning post.

In step two, a heating element is wound spirally around the positioning post.

In step three, the positioning post wound with the heating element is placed into a mold, a first layer of ceramic material is injection molded on a surface of the heating element and then cured.

In step four, the positioning post is removed from the cured first layer of ceramic material.

In step five, the cured first layer of ceramic material is sintered, thus a liquid absorption element made of porous ceramic and a heating element embedded in an interior of the liquid absorption element are obtained.

According to the foregoing method, the heating wire is sintered and embedded into the liquid absorption element made of porous ceramic, which brings the following advantages: the heating wire can be supported by the liquid absorption element, such that the diameter thereof can be smaller. In the case of the same resistance value, the smaller the diameter, the shorter the length, therefore, the overall volume will be reduced. This on the one hand can save the materials, and more importantly, the components can be miniaturized. The volume of the liquid absorption element wrapping the heating wire can be reduced, thus the rate of temperature rise of the entire liquid absorption element can be increased.

Figure 3B:
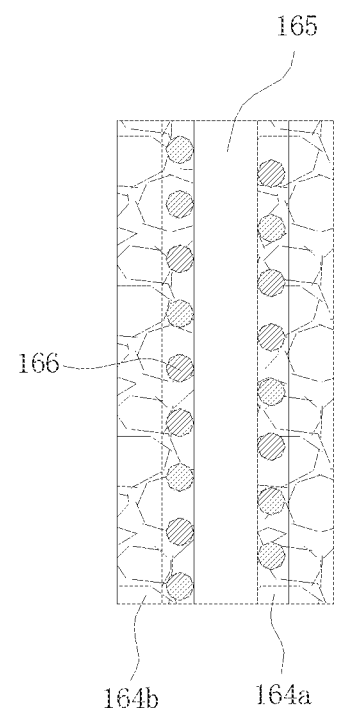
FIG. 3B is an enlarged cross-sectional view of an atomizing assembly according to another embodiment.

Referring to FIG. 3B, in an alternative embodiment, the liquid absorption element 164 includes a first layer 164a positioned proximately to the atomizing passage 165 and a second layer 164b positioned away from the atomizing passage 165. The first layer 164a and the second layer 164b are made of different materials, and the first layer 164a has a higher thermal conductivity than a thermal conductivity of the second layer 164b. The heating element 166 is embedded in the first layer 164a of the liquid absorption element 164. This configuration also allows for lowering the temperature of the liquid absorption surface of the liquid absorption element 164, thus saving energy and improving the user experience.

According to an embodiment, a method of manufacturing an atomizing assembly includes the following steps:

In step one, a positioning element is provided, the positioning element has a positioning post.

In step two, a heating element is wound spirally around the positioning post.

In step three, the positioning post with the heating element is placed into a mold, a first layer of ceramic material is injection molded on a surface of the heating element and then cured.

In step four, a second layer of ceramic material is injected on the surface of the first layer of ceramic material and then cured. The first layer of ceramic material has a higher thermal conductivity than a thermal conductivity of the second layer of ceramic material.

In step five, the positioning post is removed from the cured first and second layers of ceramic material.

In step six, the cured first and second layers of ceramic material are sintered, thus a liquid absorption element made of porous ceramic and a heating element embedded in an interior of the liquid absorption element are obtained.

Referring to FIG. 1, the power source 180 includes an electrode holder 184 and a battery (not shown). Both ends of the heating element 166 are coupled to the electrode holder 184 of the power source 180 via two wires 182. The battery is used for providing power for the heating element 166. It is to be understood that, the power source 180 may also include conventional elements such as a sensor, an indicator, etc., which are not elaborated herein.

Figure 4:
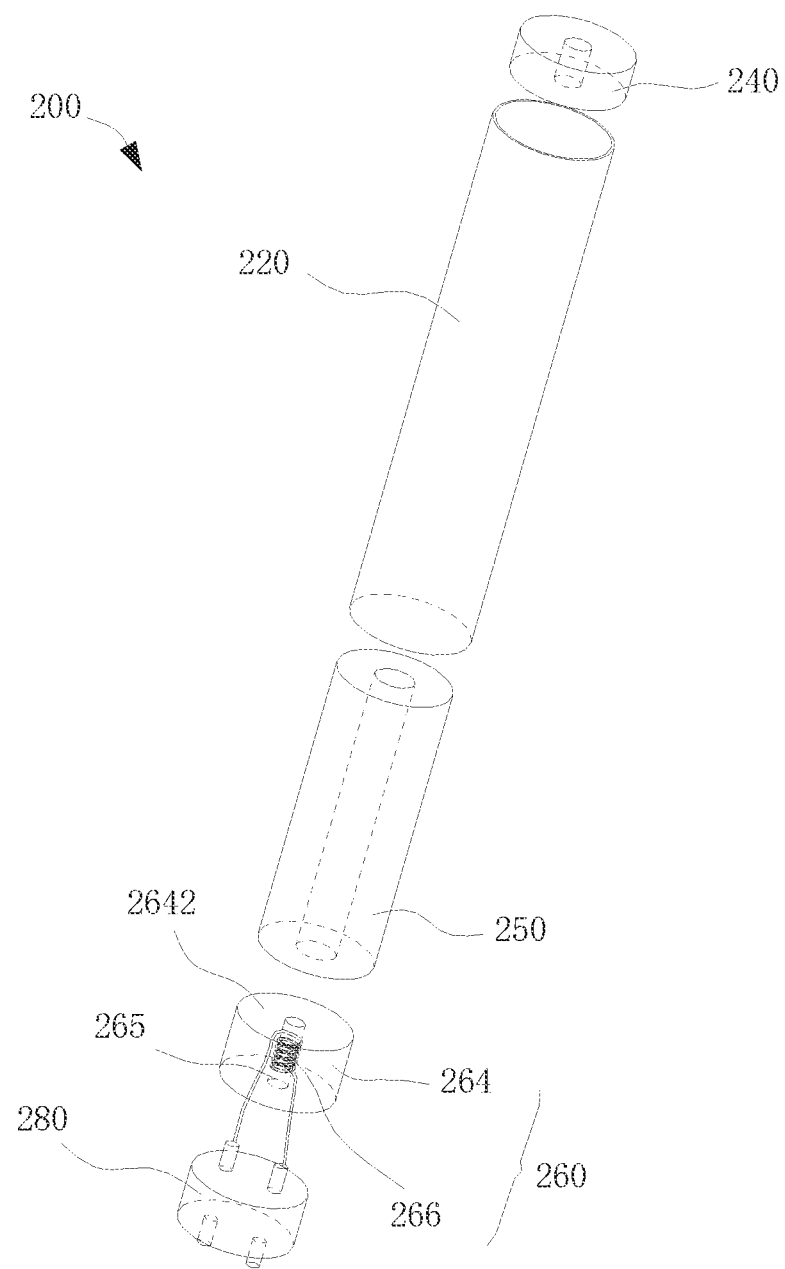
FIG. 4 is a perspective view of an electronic cigarette according to a second embodiment.
Figure 5:
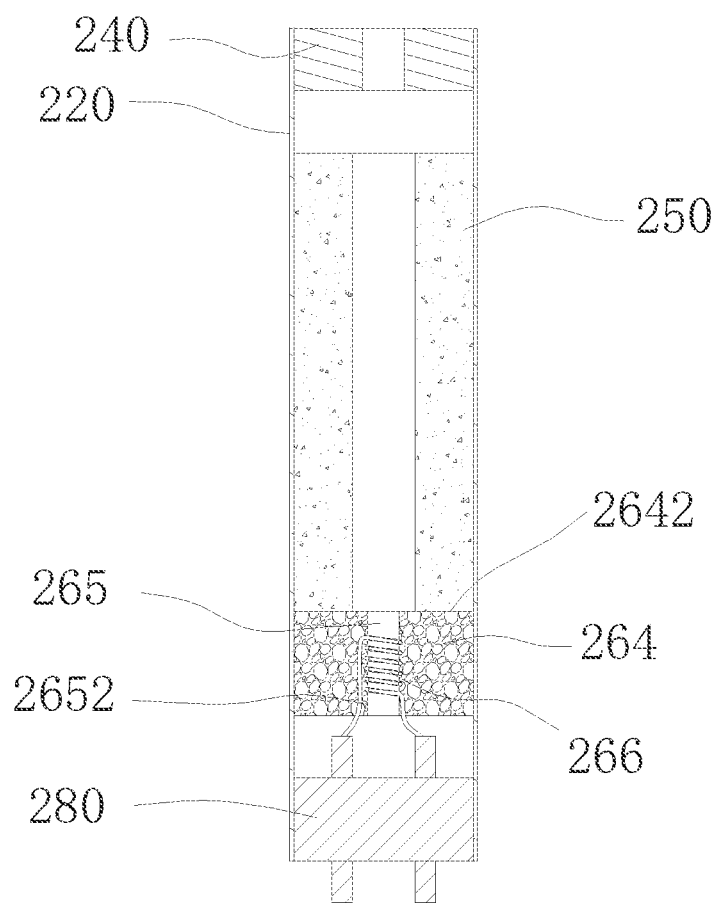
FIG. 5 is a cross-sectional view of the electronic cigarette of FIG. 4.

Referring to FIG. 4 and FIG. 5, an electronic cigarette 200 of a second embodiment has a similar structure as that of the electronic cigarette 100 of the first embodiment and includes a housing 220, a mouthpiece 240, a liquid reservoir 250, an atomizing assembly 260, and a power source assembly 280. The differences lie in that: in the illustrated embodiment, the liquid absorption element 264 is shaped substantially as a circular tube that matches with housing 220. The liquid absorption element 264 is received in the housing 220 and is located at an end of the liquid reservoir 250. The liquid absorption element 264 has a liquid absorption surface 2642 facing the liquid reservoir 250 and configured to absorb the liquid. The liquid from the liquid reservoir 250 can be uniformly dispersed in the interior and surface of the liquid absorption element 264 via the liquid absorption surface 2642 by capillary action. The liquid absorption element 264 defines an internal atomizing passage 265 in an axial direction in communication with the channel 251. The heating element 266 is a spiral tubular heating wire, which is embedded in an interior of the liquid absorption element 264. The heating element 266 spirally surrounds the atomizing passage 265, and an edge of the heating element 266 is internally tangent (aligned) to the atomizing surface 2652. Compared with the first embodiment, the liquid absorption element 264 of the second embodiment is located at the end of the liquid reservoir 250, thus it can facilitate the installation.

Figure 6:
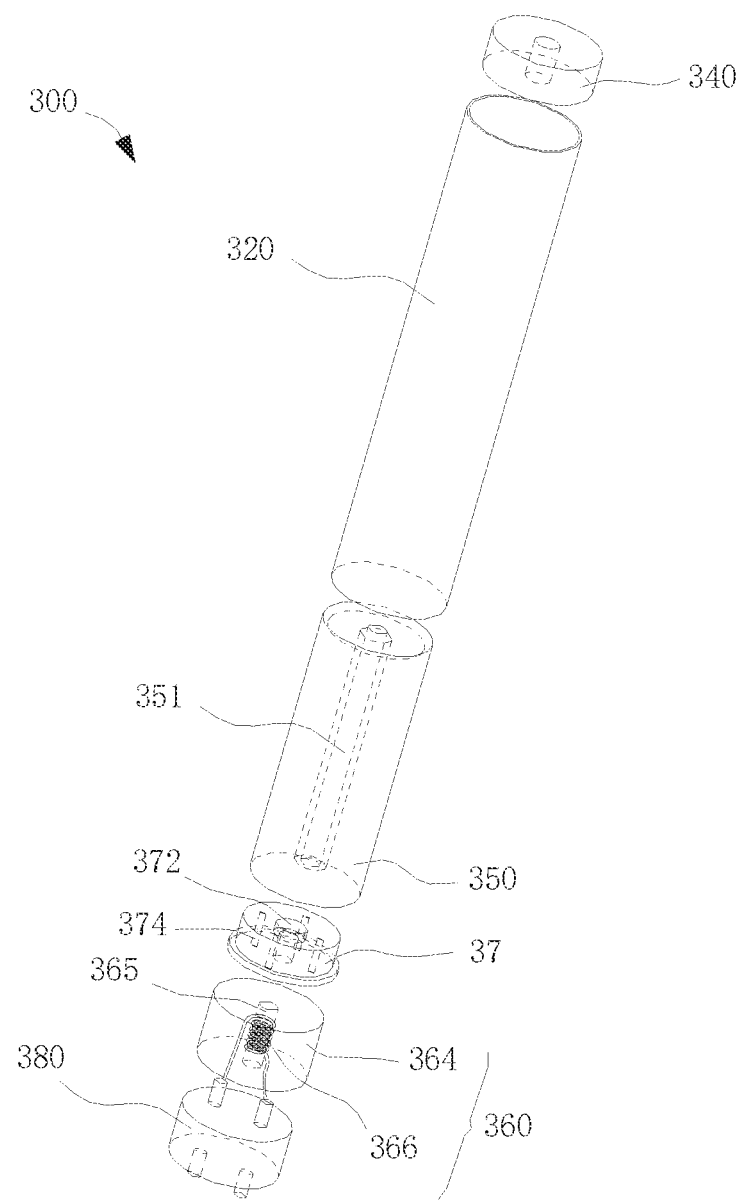
FIG. 6 is a perspective view of an electronic cigarette according to a third embodiment.
Figure 7:
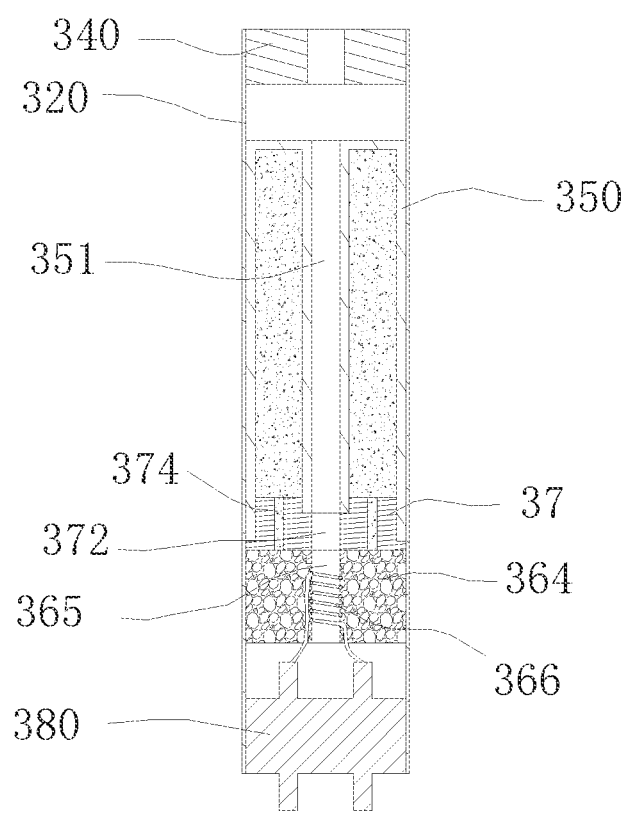
FIG. 7 is a cross-sectional view of the electronic cigarette of FIG. 6.

Referring to FIG. 6 and FIG. 7, an electronic cigarette 300 of a third embodiment has a similar structure as that of the electronic cigarette 200 of the second embodiment and includes a housing 320, a mouthpiece 340, a liquid reservoir 350, an atomizing assembly 360, and a power source assembly 380. The differences lie in that: the electronic cigarette 300 further includes a reservoir cover 37 positioned between the liquid reservoir 350 and the liquid absorption element 364. The reservoir cover 37 is shaped substantially as a round cover and is located at an end of the liquid reservoir 350 to seal the liquid reservoir 350. The reservoir cover 37 defines an airflow channel 372 in a middle portion thereof in communication with the channel 351. The reservoir cover 37 further defines four liquid conduction channels 374 evenly distributed around the airflow channel 372. No liquid medium is provided in the reservoir 350, and the liquid in the liquid reservoir 350 can flow into the liquid absorption element 364 via the four liquid conduction channels 374. The liquid absorption element 364 defines an internal atomizing passage 365 in an axial direction in communication with the airflow channel 372. The heating element 366 is a spiral tubular heating wire, which is embedded in an interior of the liquid absorption element 364. Compared with the second embodiment, the liquid of the third embodiment can flow into the liquid absorption element 364 via the liquid conduction channels 374, such that the flow of liquid can be more accurately controlled. It should be noted that, the number of the liquid conduction channels 374 can be three, five or more.

Figure 8:
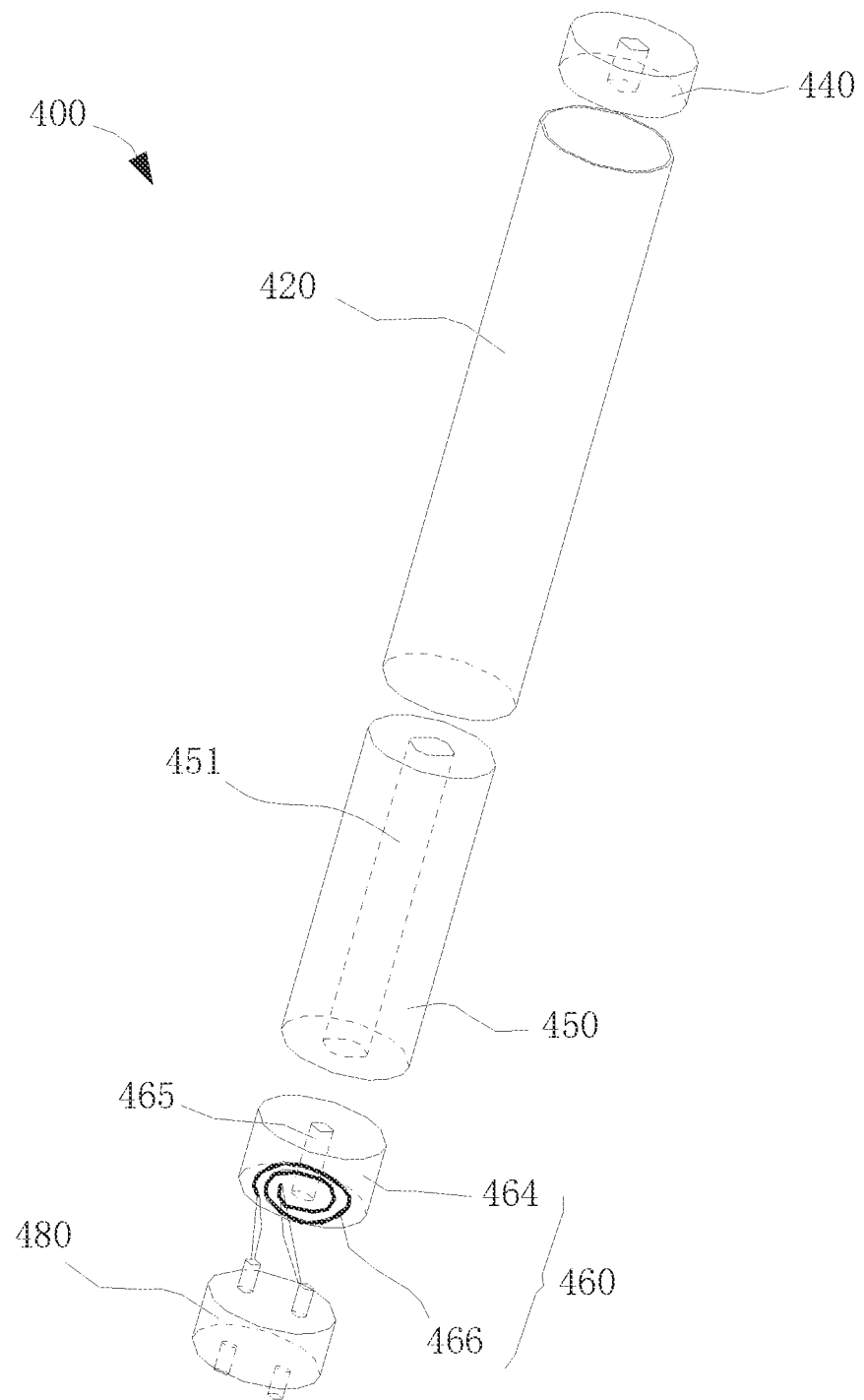
FIG. 8 is a perspective view of an electronic cigarette according to a fourth embodiment.
Figure 9:
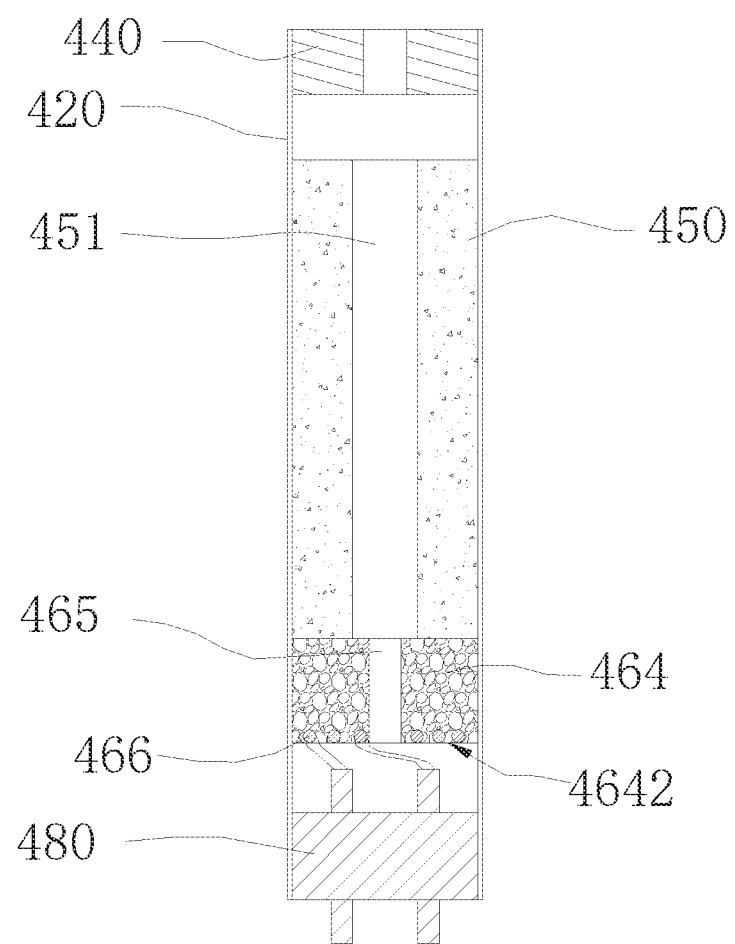
FIG. 9 is a cross-sectional view of the electronic cigarette of FIG. 8.

Referring to FIG. 8 and FIG. 9, an electronic cigarette 400 a fourth embodiment is similar to the electronic cigarette 200 of the second embodiment. The electronic cigarette 400 includes a housing 420, a mouthpiece 440, a liquid reservoir 450, an atomizing assembly 460, and a power source assembly 480. The difference lies in that: the atomizing surface 4642 is an end surface of the liquid absorption element 464 away from the liquid reservoir 450. The heating element 466 is a planar spiral heating wire having Archimedes spiral. The heating element 466 is embedded in an interior of the liquid absorption element 464 and is located at an end of the liquid absorption element 464 away from the liquid reservoir 450. The heating element 466 spirally surrounds the atomizing passage 465, and an edge of the heating element 466 is internally tangent (aligned) to the atomizing surface 4642. When the heating element 466 is powered, the liquid absorption element 464 can be heated by the heating element 466 from one end thereof, such that the liquid stored inside the liquid absorption element 464 will be uniformly heated and atomized into uniform vapor particles (i.e. smoke). The smoke enters the atomizing passage 465 through the atomizing surface 4642, and then enters the channel 451, and finally inhaled by the user via the air outlet.

In one embodiment, a method of manufacturing the aforementioned atomizing assembly includes the following steps:

In step one, a positioning element is provided. The positioning element includes a positioning surface and a positioning post located on the positioning surface.

In step two, a heating element being a planar helical heating wire is placed on the positioning surface and surrounds the positioning post;

In step three, the positioning post with the heating element is placed into a mold, a first layer of ceramic material is injection molded on a surface of the heating element and then cured;

In step four, the positioning post is removed from the cured first layer of ceramic material;

In step five, the cured first layer of ceramic material is sintered, thus obtaining a liquid absorption element made of porous ceramic and a heating element embedded at an end of the liquid absorption element.

Figure 10:
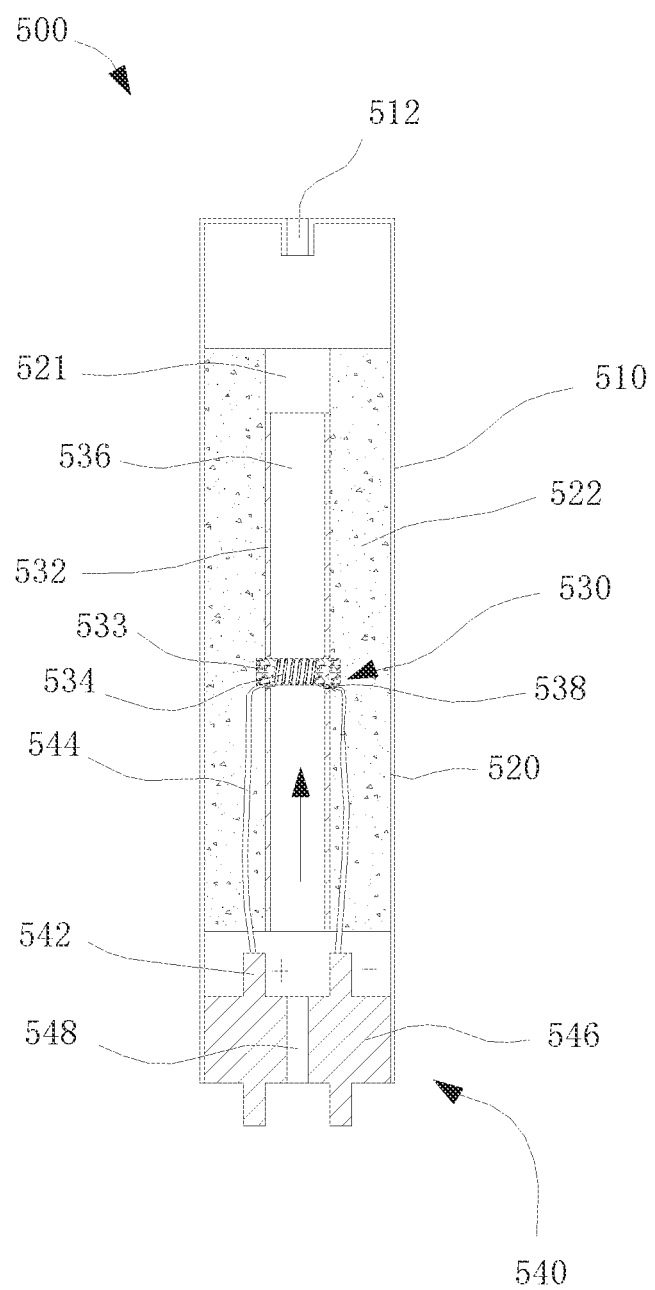
FIG. 10 is a perspective view of an electronic cigarette according to a fifth embodiment.

Referring to FIG. 10, an electronic cigarette 500 in accordance with a fifth embodiment includes a housing 510, a liquid reservoir 520, an atomizing assembly 530, and a power source assembly 540. The liquid reservoir 520, the atomizing assembly 530, and the power source assembly 540 are received in the housing 510. The power source assembly 540 is configured to provide power for the atomizing assembly 530.

The housing 510 has a substantially cylindrical shape, that is, a circular cross section. The housing 510 defines a cavity for accommodating each internal element of the electronic cigarette 500. The housing 510 is made of plastic. In alternative embodiments, the housing 510 can have a rectangular or oval cross-section. One end of the housing 510 defines an air outlet 512 at an end thereof and an air inlet (not shown) at the other end thereof. The housing 510 has a hollow structure. The housing 510 can be provided with a filter nozzle at the end thereof adjacent to the air outlet 512 for filtering nicotine and nicotinamide in the smoke.

The liquid reservoir 520 is received in the housing 510 and sleeved on the outside of the atomizing assembly 530. In the illustrated embodiment, the liquid reservoir 520 has a cylindrical shape and defines a channel 521 along an axial direction in a middle portion thereof, which is in communication with the air inlet and the air outlet 512. The liquid reservoir 520 is internally filled with a liquid storage medium 522 for storing liquid. The liquid storage medium 522 can be made of liquid absorbent materials, such as fiber, foam, sponge, foam ceramic, soft rubber or silicon. The material forming the liquid reservoir 520 may have elasticity, such that during assembly, the liquid reservoir 520 may be in sufficient contact with the surface of the atomizing assembly 530 by an external force such as pressing. According to the principle of concentration balance, the liquid stored in the liquid reservoir 520 can be delivered to the atomizing assembly 530 with liquid absorbing capability.

The atomizing assembly 530 is received in the housing 510. The atomizing assembly 530 includes a support element 532, a liquid absorption element 533, and a heating element 534. The liquid absorption element 533 is disposed on the support element 532 and extends through the support element 532.

The support element 532 has a hollow cylindrical structure and is received in the channel 521. The support element 532 defines an atomizing passage 536 therein in communication with the channel 521 to allow the gas to flow through. The support element 532 further defines two aligned through holes 538 on a middle portion of the sidewall thereof, the two through holes 538 are used to support and fix the liquid absorption element 533. The through holes 538 are in communication with the atomizing passage 536. It should be understood that, the number of the through holes 538 can be one or more than two.

Figure 11:
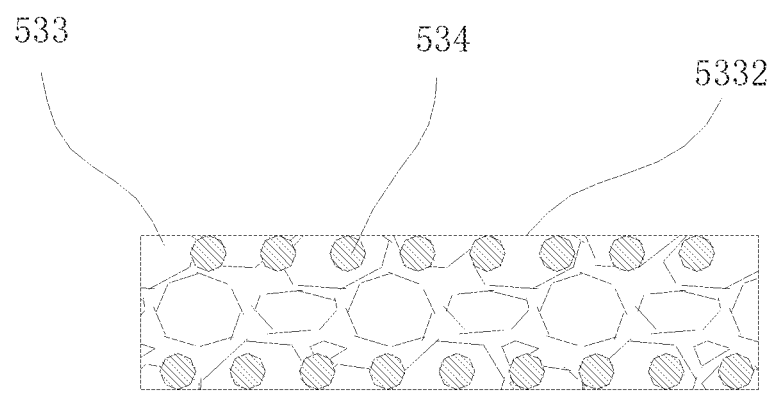
FIG. 11 is an enlarged cross-sectional view of an atomizing assembly of FIG. 10.

Referring to FIG. 11, the liquid absorption element 533 is shaped substantially as a solid cylinder that matches with the through holes 538. Accordingly, both ends of the liquid absorption element 533 can extend through the through holes 538 of the support element 532, respectively, therefore the liquid absorption element 533 can extend inside the liquid reservoir 520 to be in direct contact with the liquid storage medium 522. A middle portion of the liquid absorption element 533 is positioned inside the atomizing passage 536, and the liquid absorption element 533 has an atomizing surface 5332 within the atomizing passage 536. The liquid absorption element 533 can be made of a porous ceramic material with liquid storage capability and high temperature resistance. In the illustrated embodiment, the liquid absorption surface of the liquid absorption element 533 are at both ends of the liquid absorption element 533, which include both end surfaces and partial outer circumferential surface.

The heating element 534 is a spiral tubular heating wire embedded in an interior of the liquid absorption element 533, and the heating wire helically surrounds an axis of the liquid absorption element 533. In the illustrated embodiment, an edge of the heating element 534 is internally tangent (aligned) to the atomizing surface 5332. The heating element 534 is made of a conductive material, such as flexible metals or alloys, preferably nichrome wire. When the heating element 534 is powered, the liquid absorption element 533 can be heated by the heating element 534, such that the liquid stored inside the liquid absorption element 533 will be uniformly heated and atomized into uniform vapor particles (i.e. smoke). The smoke enters the atomizing passage 536 through the atomizing surface 5332, and then enters the channel 521, and finally inhaled by the user via the air outlet 512.

Referring to FIG. 10, the power source assembly 540 is electrically coupled to the heating element 534, so as to provide power for the heating element 534. In the illustrated embodiment, the power supply assembly 540 includes an electrode 542, a conductive wire 544, an electrode holder 546, and a battery (not shown). The electrode 542 is electrically coupled to the heating element 534 through the conductive wire 544. The electrode 542 is fixed on the electrode holder 546. The electrode holder 546 defines an air intake 548 to allow the air to pass through. In an alternative embodiment, the electrode holder 546 can be omitted.

Figure 12:
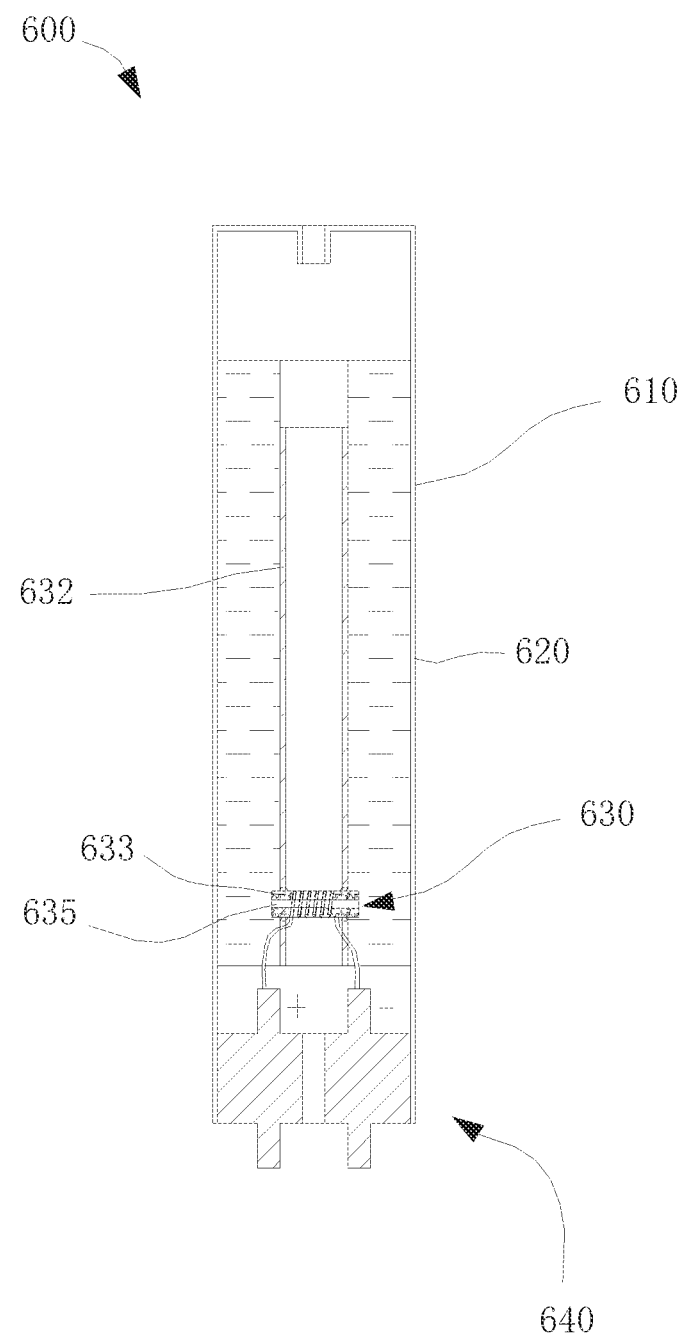
FIG. 12 is a perspective view of an electronic cigarette according to a sixth embodiment.
Figure 13:
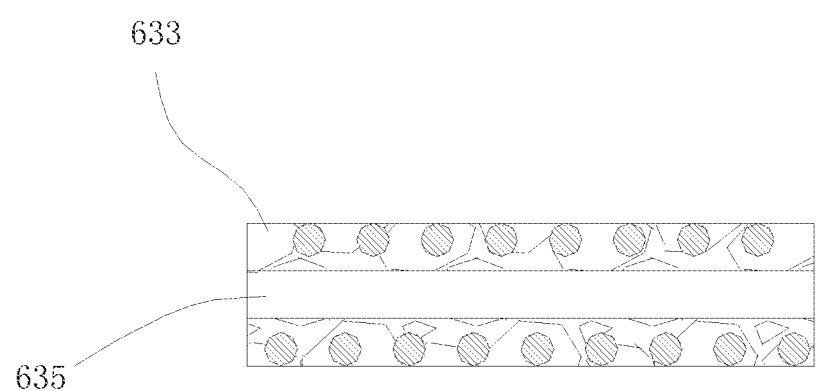
FIG. 13 is a cross-sectional view of the electronic cigarette of FIG. 12.

Referring to FIG. 12 and FIG. 13, an electronic cigarette 600 according to a sixth embodiment has a similar structure as that of the electronic cigarette 500 of the fifth embodiment and includes a housing 610, a liquid reservoir 620, an atomizing assembly 630, and a power source assembly 640. The difference lies in that:

(1) No storage medium is filled in the liquid reservoir 620, and the liquid is directly stored in the liquid reservoir 620.

(2) The liquid absorption element 633 is located at a position of the support element 632 adjacent to the power source assembly 640.

(3) The liquid absorption element 633 has a tubular tube shape and axially defines a liquid passage 635 therein. The atomizing surface is an outer circumferential surface of the liquid absorption element 633, and the liquid absorption surface is an inner circumferential surface of the liquid absorption element 633, i.e., the liquid absorption surface is a sidewall of the liquid passage 635.

The liquid absorption element 533 of the fifth embodiment absorbs and stores liquid in the liquid storage medium 522 mainly through two ends thereof, thus the liquid conduction rate may be relatively slow. The liquid reservoir 620 of the sixth embodiment directly contains the liquid, and the atomizing assembly 630 is positioned downwardly, and the liquid passage 634 is axially defined in the liquid absorption element 633, such that the contact area with the liquid is increased, thus increasing the liquid conduction rate.

Although the respective embodiments have been described one by one, it shall be appreciated that the respective embodiments will not be isolated. Those skilled in the art can apparently appreciate upon reading the disclosure of this application that the respective technical features involved in the respective embodiments can be combined arbitrarily between the respective embodiments as long as they have no collision with each other. Of course, the respective technical features mentioned in the same embodiment can also be combined arbitrarily as long as they have no collision with each other.

It should be noted that, the configuration how the liquid absorption surface for absorbing liquid and the atomizing surface for the heating element are positioned on the liquid absorption element are not limited hereto. The number of the liquid absorption surfaces may be one or more, and the number of the atomizing surfaces may also be one or more.

Although the description is illustrated and described herein with reference to certain embodiments, the description is not intended to be limited to the details shown. Modifications may be made in the details within the scope and range equivalents of the claims.

What is claimed is:

1. A method of manufacturing an atomizing assembly, comprising:
   providing a positioning element, the positioning element comprising a positioning post;
   winding a heating element spirally around the positioning post;
   placing the positioning post wound with the heating element into a mold, injection molding a first layer of ceramic material on a surface of the heating element and then curing;
   removing the positioning post from the cured first layer of ceramic material; and
   sintering the cured first layer of ceramic material, thus obtaining a liquid absorption element made of porous ceramic and a heating element embedded in an interior of the liquid absorption element.

2. The method according to claim 1, wherein the liquid absorption element has a tubular shape, the liquid absorption element defines an atomizing passage therein, the atomizing surface is a sidewall of the atomizing passage, and the heating element is a spiral tubular heating wire, which spirally surrounds the atomizing passage.

3. The method according to claim 2, wherein a distance between the heating wire to the atomizing surface is less than a distance between the heating wire to the liquid absorption surface of the liquid absorption element.

4. The method according to claim 2, wherein a thermal conductivity of the liquid absorption element is gradually reduced from inside to outside along a radial direction.

5. The method according to claim 1, wherein the porous ceramic has a porosity of 30% to 60%.

6. The method according to claim 1, wherein after injecting the first layer of ceramic material on the surface of the heating element, the method further comprises: injection molding a second layer of ceramic material on the surface of the first layer of ceramic material, wherein the first layer of ceramic material has a higher thermal conductivity than a thermal conductivity of the second layer of ceramic material.

7. The method according to claim 1, wherein the positioning element further comprises a positioning surface, the positioning post is located on the positioning surface, the heating element is a planar helical heating wire placed on the positioning surface and surrounding the positioning post.

8. A method of manufacturing an atomizing assembly, comprising:
 providing a positioning element, the positioning element comprising a positioning post;
 winding a heating element spirally around the positioning post;
 placing the positioning post wound with the heating element into a mold, injection molding a first layer of ceramic material on a surface of the heating element and then curing;
 injection molding a second layer of ceramic material on a surface of the first layer of ceramic material and then curing, wherein the first layer of ceramic material has a higher thermal conductivity than a thermal conductivity of the second layer of ceramic material;
 removing the positioning post from the cured first layer of ceramic material; and
 sintering the cured first and second layers of ceramic material, thus obtaining a liquid absorption element made of porous ceramic and a heating element embedded in an interior of the liquid absorption element.

9. The method according to claim 8, wherein the liquid absorption element has a tubular shape, the liquid absorption element defines an atomizing passage therein, the atomizing surface is a sidewall of the atomizing passage, and the heating element is a spiral tubular heating wire, which spirally surrounds the atomizing passage.

10. The method according to claim 9, wherein a distance between the heating wire to the atomizing surface is less than a distance between the heating wire to the liquid absorption surface of the liquid absorption element.

11. The method according to claim 9, wherein the liquid absorption element comprises a first layer proximately to the atomizing passage and a second layer away from the atomizing passage, the first layer has a higher thermal conductivity than a thermal conductivity of the second layer, the heating element is embedded in the first layer of the liquid absorption element.

12. The method according to claim 8, wherein the porous ceramic has a porosity of 30% to 60%.

13. A method of manufacturing an atomizing assembly, comprising:
 providing a positioning element, the positioning element comprising a positioning surface and a positioning post located on the positioning surface;
 placing a heating element being a planar helical heating wire on the positioning surface and surrounds the positioning post;
 placing the positioning post with the heating element into a mold, injection molding a first layer of ceramic material on a surface of the heating element and then curing;
 removing the positioning post from the cured first layer of ceramic material; and
 sintering the cured first layer of ceramic material, thus obtaining a liquid absorption element made of porous ceramic and a heating element embedded in an end of the liquid absorption element.

14. The method according to claim 13, wherein the porous ceramic has a porosity of 30% to 60%.

* * * * *